(12) United States Patent
Mecca et al.

(10) Patent No.: US 8,434,422 B2
(45) Date of Patent: May 7, 2013

(54) COATING APPARATUS AND METHOD

(75) Inventors: Jodi M. Mecca, Midland, MI (US); Paul L. Morabito, Midland, MI (US); Carol E. Lyons-Bell, Freeland, MI (US); James G. Williams, Sanford, MI (US)

(73) Assignee: Dow Global Technologies LLC, Midland, MI (US)

( * ) Notice: Subject to any disclaimer, the term of this patent is extended or adjusted under 35 U.S.C. 154(b) by 476 days.

(21) Appl. No.: 12/759,026

(22) Filed: Apr. 13, 2010

(65) Prior Publication Data
US 2010/0266773 A1 Oct. 21, 2010

Related U.S. Application Data

(60) Provisional application No. 61/170,842, filed on Apr. 20, 2009.

(51) Int. Cl.
*B05C 11/04* (2006.01)

(52) U.S. Cl.
USPC ............................. 118/200; 118/206; 118/256

(58) Field of Classification Search .................. 118/200, 118/206, 256
See application file for complete search history.

(56) References Cited

U.S. PATENT DOCUMENTS

| | | | |
|---|---|---|---|
| 5,157,820 A * | 10/1992 | Frederick | 29/25.42 |
| 6,296,702 B1 * | 10/2001 | Bryning et al. | 118/401 |
| 6,689,218 B2 | 2/2004 | Potyralio et al. | |
| 6,756,074 B2 | 6/2004 | Potyrailo et al. | |
| 2003/0224205 A1 | 12/2003 | Li et al. | |
| 2005/0217818 A1 | 10/2005 | Breiten et al. | |
| 2006/0083664 A1 | 4/2006 | Bahr | |

FOREIGN PATENT DOCUMENTS

| | | |
|---|---|---|
| WO | 0102097 A1 | 1/2001 |
| WO | 2004073048 A2 | 8/2004 |
| WO | 2006110153 | 10/2006 |
| WO | 2008136833 | 11/2008 |

OTHER PUBLICATIONS

Meredith et al., "High Throughput Measurement of Polymer Blend Phase Behavior", Macromolecules, 2000, pp. 5760-5762, vol. 33, American Chemical Society.
Chisholm et al., "Combinatorial Chemistry Methods for Coating Development V. The Importance of Understanding Process Capability", Progress in Organic Coatings, 2003, pp. 120-127, vol. 47.
Iden et al., "Combinatorial Materials Research in the Polymer Industry: Speed Versus Flexibility", Macromolecular Rapid Communications, 2003, pp. 63-72, vol. 24, Wiley-VCH Verlag GmbH & Co. KGaA.
Cawse et al., "Combinatorial Chemistry Methods for Coating Development V: Generating a Combinatorial Array of Uniform Coatings Samples", Progress in Organic Coatings, 2003, pp. 128-135, vol. 47, Elsevier B.V.
Madrigal, Luis, "Development of Environmentally Friendly Surfactants for Architectural Paint Applications—Using High Throughput Development", European Coating Show Mar. 31, 2009.

\* cited by examiner

*Primary Examiner* — Dah-Wei Yuan
*Assistant Examiner* — Stephen Kitt
(74) *Attorney, Agent, or Firm* — Cantor Colburn LLP; Karl E. Stauss

(57) ABSTRACT

The present invention generally relates to a coating apparatus and method for substantially simultaneously forming a plurality of coatings on a substrate and to a method of analyzing at least one characteristic or property of the coatings.

18 Claims, 4 Drawing Sheets

COATING APPARATUS AND METHOD

CROSS-REFERENCE TO RELATED APPLICATIONS

This application claims benefit from U.S. Provisional Patent Application No. 61/170,842, filed 20 Apr. 2009, the entire contents of which are hereby incorporated by reference herein.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The invention generally relates to a coating apparatus and method for substantially simultaneously forming a plurality of coatings on a substrate and to a method of analyzing at least one characteristic or property of the coatings.

2. Description of Related Art

There is a need in the coating art for a coating apparatus and method for substantially simultaneously forming a plurality of coatings on a substrate. There is also a need in the coating art for a method of analyzing at least one characteristic or property of the coatings. Preferably the coating apparatus is useful in and the methods comprise high throughput coating or coating analysis workflows, or both. Such high throughput workflows would be especially useful as a means for accelerating coating research and development.

BRIEF SUMMARY OF THE INVENTION

In a first embodiment, the present invention provides a coating apparatus (invention coating apparatus), the coating apparatus being for substantially simultaneously forming a plurality of coatings on a substrate, the coatings being disposed in a two-dimensional arrangement thereon, the coating apparatus comprising a spreader assembly, basal support member, and one or more spacers, wherein:
(a) the spreader assembly is for substantially simultaneously spreading at least four liquid coating precursors in a two-dimensional arrangement on a substrate, the spreader assembly comprising a plate and a plurality of spreading means:
(i) the plate having spaced apart top and bottom surfaces, spaced apart sides, and defining a plurality of apertures therethrough between the top and bottom surfaces, the apertures being disposed in a two-dimensional arrangement and dimensioned for allowing dispensing of the liquid coating precursors through the apertures in the plate and onto the substrate and the plurality of spreading means being less than, equal to, or greater than the plurality of apertures in the plate, and
(ii) the plurality of spreading means extending downwardly from the bottom surface of, and being in operative connection with, the plate so that each spreading means, or a portion thereof, is disposed proximal to a different one of the apertures, or a portion thereof, in the plate;
(b) the basal support member comprising a guide member for defining a coating direction, the basal support member defining at least one aperture therein, the at least one aperture being disposed for receiving the plurality of spreading means of the spreader assembly; and
(c) each spacer being disposed in direct physical contact with the spreader assembly and the basal support member, thereby establishing a spaced-apart distance between the substrate and the plurality of spreading means.

In a second embodiment, the present invention provides a method (invention method) of substantially simultaneously forming a plurality of test coatings on a substrate, the test coatings being disposed in a two-dimensional arrangement thereon, the method comprising steps of: (a) disposing the coating apparatus of the first embodiment above a coating-ready surface of a substrate; (b) dispensing through apertures of the spreader assembly of the coating apparatus of the first embodiment at least four liquid coating precursors onto the coating-ready surface of the substrate to give a precursor-prepared substrate having the at least four liquid coating precursors dispensed thereon in a two-dimensional arrangement; and (c) moving the spreader assembly of the coating apparatus relative to the precursor-prepared substrate so as to substantially simultaneously contact and spread the liquid coating precursors on the coating-ready surface of the substrate, thereby forming at least four test coatings on the coating-ready surface of the substrate, the test coatings being disposed thereon in the two-dimensional arrangement.

Preferably, the method of the second embodiment further comprises a step of: (d) independently evaluating at least one characteristic or property of the test coatings. The evaluating step (d) can be conducted immediately after the moving step (c). Preferably, the test coatings are allowed to cure, dry, or both for a time before conducting the evaluating step (d) with them.

The coating apparatus and method of the first and second embodiments, respectively, provide a means of substantially simultaneously forming a plurality of test coatings on a substrate. In some embodiments, the coating apparatus is used in and the method comprises a high throughput coating workflow. In some embodiments, the invention method further provides a means of analyzing at least one characteristic or property of the test coatings in a high throughput coating analysis workflow. Thus, the invention coating apparatus and method provides, among other things, a means for accelerating coating research and development.

The test coatings on the substrate prepared according to the method of the second embodiment can be used for any purpose such as, for example, as commercial display samples (e.g., of paint colors); as materials for analysis in coating research and development (e.g., analysis of characteristics such as, for example, color and gloss, of physical properties such as, for example, degree of hardness and resistance to cracking (e.g., mud cracking), minimum film formation temperature, and low temperature coalescence, of chemical properties such as, for example, adhesive bonding strength, blocking, solubility, dirt pick-up resistance, and stain resistance, or of a combination thereof); and as adhesive applications for bonding the substrate to another material.

Additional embodiments are described in accompanying drawing(s) and the remainder of the specification, including the claims.

BRIEF DESCRIPTION OF THE DRAWING(S)

Some embodiments of the present invention are described herein in relation to the accompanying drawing(s), which will at least assist in illustrating various features of the embodiments.

Figure 4:
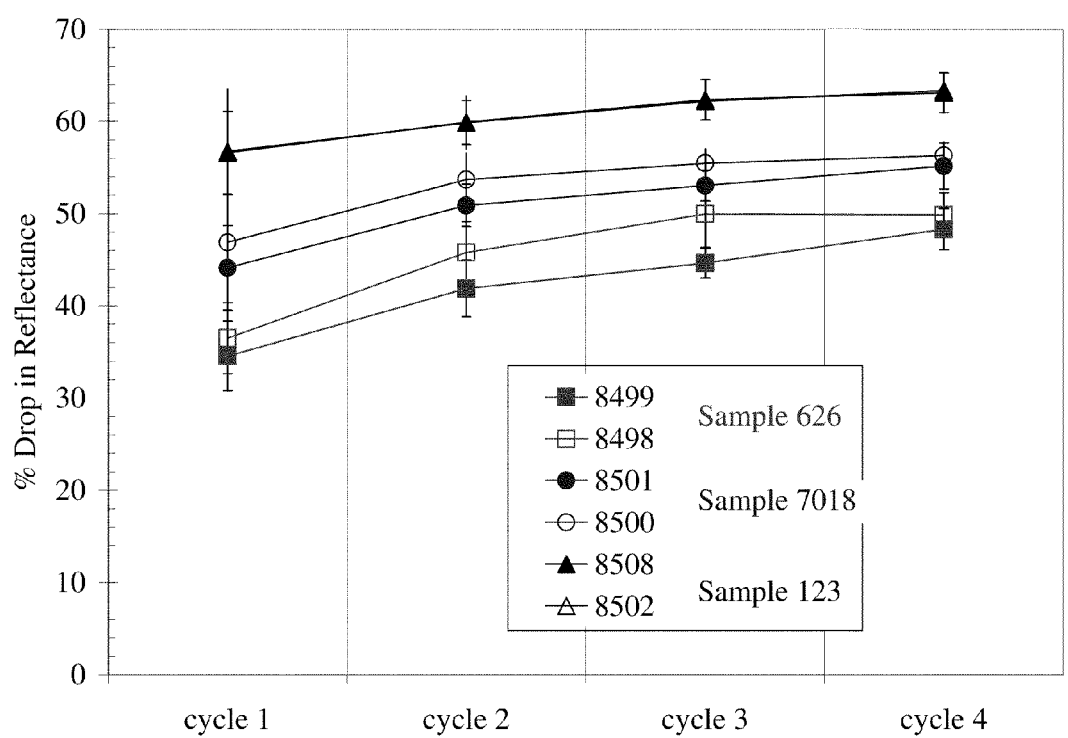

FIG. 4 plots of an average of percent drop in reflectance for measurements taken on the 24 latex paint test coatings over four dirt pick-up resistance treatment cycles.

DETAILED DESCRIPTION OF THE INVENTION

Figure 1:
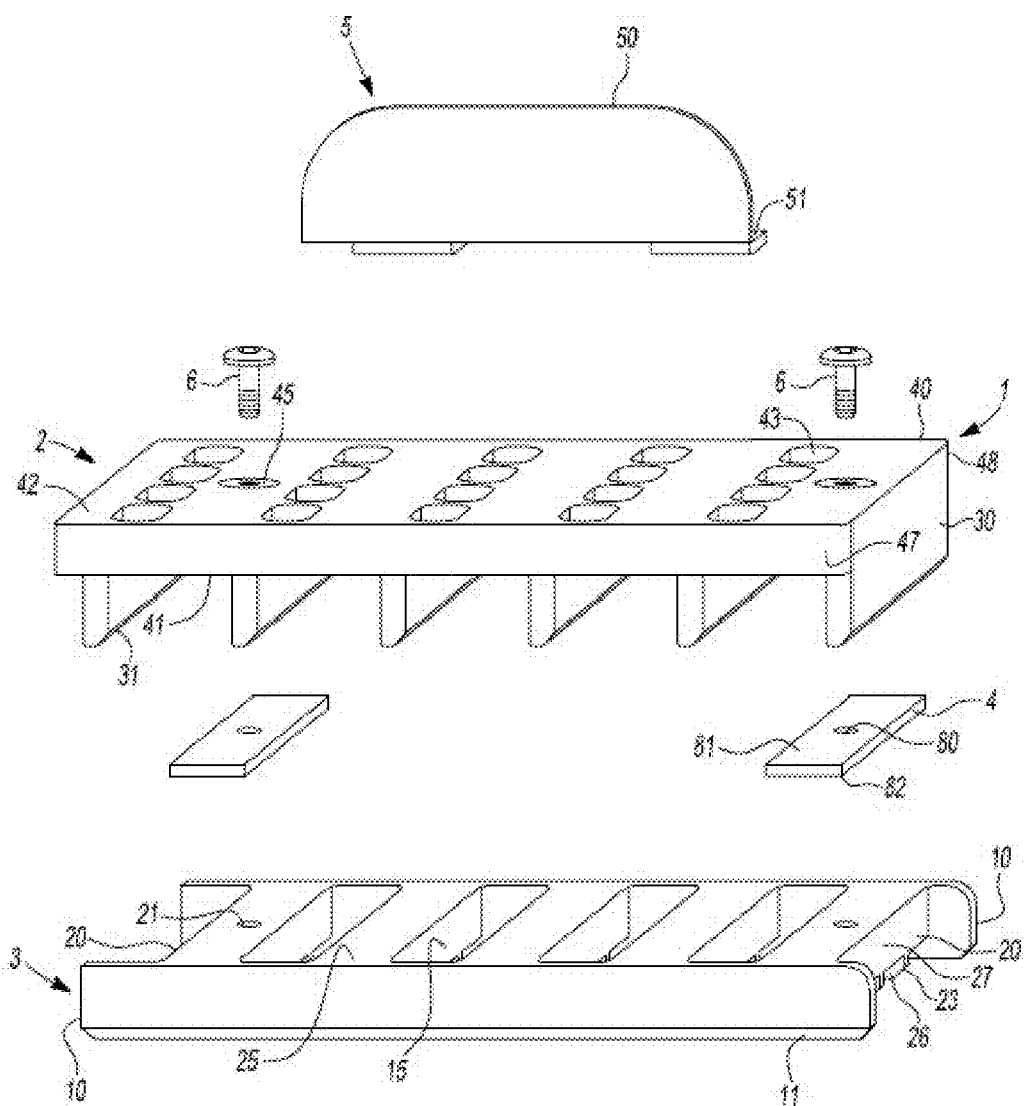
FIG. 1 depicts a partially exploded view of a preferred embodiment of the coating apparatus of the first embodiment.

As mentioned previously, FIG. 1 shows a partially exploded view of a preferred embodiment of the coating apparatus of the first embodiment, the preferred embodiment being sled-type coating apparatus 1. In FIG. 1, sled-type coating apparatus 1 comprises spreader assembly 2, basal support member 3, two shims 4, handle assembly 5, and two externally-screw-threaded fasteners 6.

Spreader assembly 2 comprises six contoured drawdown blades 30 and a plate 40. Each contoured drawdown blade 30 defines a leading surface 31, which is disposable for contacting the coating-ready surface (e.g., see FIGS. 2A and 2B) of the substrate (e.g., see FIGS. 2A and 2B) in the method of the second embodiment at an angle therebetween of from greater than 10 degrees to less than 80 degrees. Plate 40 has spaced-apart sides 47 and 48 (not shown). Plate 40 also has spaced-apart bottom surface 41 and top surface 42 and defines twenty apertures 43 therethrough between bottom surface 41 and top surface 42. Apertures 43 are disposed in plate 40 in a two-dimensional arrangement, in particular a 4-row-by-5-column predefined array. Plate 40 also defines two internally-screw-threaded apertures 45. Contoured drawdown blades 30 are spaced-apart from and generally parallel to each other and are in operative connection to bottom surface 41 of plate 40 proximal to, but spaced apart from, apertures 43 and generally perpendicular to sides 47 and 48, thereby establishing spreader assembly 2.

Basal support member 3 comprises two rail members 10, two spacer-receiving members 20, and three cross-brace members 25. Rail members 10 define beveled bottom edges 11. Spacer-receiving members 20 and cross-brace members 25 are substantially identical to each other except each spacer-receiving member 20 defines an internally-screw-threaded aperture 21, whereas cross-brace members 25 lack such an internally-screw threaded aperture. Each spacer-receiving member 20 and cross-brace member 25 defines three downwardly-extending, evenly spaced-apart protrusions 23 having bottom edges 26 (only portions of rear most protrusions 23 are visible). Each spacer-receiving member 20 and cross-brace member 25 has a leading face 27. Rail members 10 are spaced-apart and generally parallel to each other by, and are in operative connection to, spacer-receiving members 20 and cross-brace members 25 so that rail members 10 are substantially perpendicular to spacer-receiving members 20 and cross-brace members 25, and so that bottom edges 26 of protrusions 23 and beveled bottom edges 11 of rail members 10 are all simultaneously disposable in physical contact with the coating-ready surface (e.g., see FIGS. 2A and 2B) of the substrate (e.g., see FIGS. 2A and 2B) in the method of the second embodiment. Spacer-receiving members 20 and cross-brace members 25 in turn are spaced apart from each other, thereby defining four apertures 15 and establishing basal support member 3.

Shims 4 define apertures 80 and have top and bottom surfaces 81 and 82, respectively. Shims 4 are characterized by a thickness (not indicated) equal to distance t (not indicated) between top and bottom surfaces 81 and 82. Each shim 4 is an example of the spacer mentioned in the first embodiment.

Handle assembly 5 is optional. It comprises handle 50 and two mounting brackets 51. Handle 50 is disposed in operative contact to mounting brackets 51 (e.g., by welding or soldering), thereby establishing handle assembly 5.

Assemble sled-type coating apparatus 1 from the previously described spreader assembly 2, basal support member 3, two shims 4, handle assembly 5, and two externally-screw-threaded fasteners 6 as follows. Place basal support member 3 on a flat surface such that beveled bottom edges 11 of rail members 10 are in contact therewith. Dispose each shim 4 on a different spacer-receiving member 20 such that aperture 80 of shim 4 is aligned with aperture 21 of spacer-receiving member 20. Dispose spreader assembly 2 on shims 4 such that a different one of contoured drawdown blades 30 (except left-most one) is in flush physical contact with leading face 27 of a different one of spacer-receiving members 20 and cross-brace members 25 and so that apertures 45 of plate 40 align with apertures 80 of shims 4 and apertures 21 of spacer-receiving members 20. Threadably engage externally-screw-threaded fasteners 6 sequentially through apertures 45 of plate 40, apertures 80 of shims 4, and apertures 21 of spacer-receiving members 20 so as to secure spreader assembly 2, shims 4, and basal support member 3 in sequential operative connection, thereby establishing a preferred handleless sled-type coating apparatus of the first embodiment. If desired, dispose handle assembly 5 onto and in operative connection to (e.g., by welding or soldering) top surface 42 of plate 40 so that brackets 51 are spaced apart from apertures 43, thereby establishing sled-type coating apparatus 1.

Figure 2A:
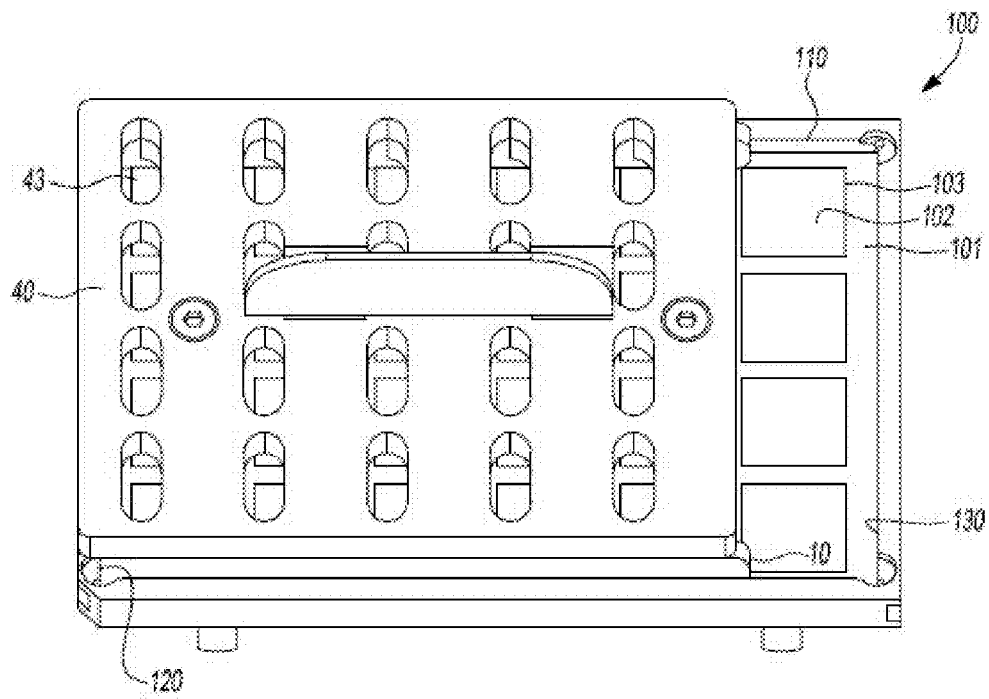
FIGS. 2A and 2B depict perspective views at respectively starting and finishing positions of a preferred coating apparatus-substrate holder assembly employing the preferred embodiment of the coating apparatus FIG. 1.
Figure 2B:
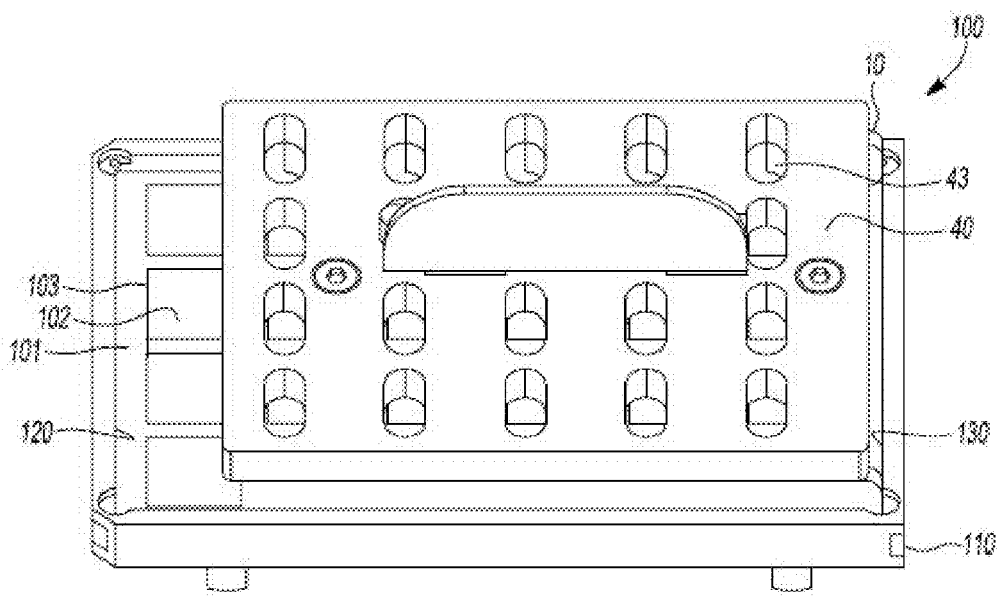

As mentioned previously, FIGS. 2A and 2B depict perspective views at respectively starting and finishing positions of a preferred coating apparatus-substrate holder assembly employing the preferred embodiment of the coating apparatus FIG. 1. In FIGS. 2A and 2B, coating apparatus-substrate holder assembly 100 comprises sled-type coating apparatus 1 (see FIG. 1) and frame substrate holder 110. (Sled-type coating apparatus 1 (see FIG. 1) is shown in FIGS. 2A and 2B in the same left-to-right orientation as it is shown in FIG. 1.) Beveled bottom edges 11 of rail members 10 (see FIG. 1) are disposed within substrate holder 110. A substrate 101 having coating ready surface 102 divided into a plurality of hypothetical target squares 103 is disposed within substrate holder 110 such that coating-ready surface 102 is spaced-apart by distance t (not shown) from contoured drawdown blades 30 (see FIG. 1) of spreader assembly 2 (see FIG. 1). Liquid coating precursors (not shown) can be dispensed through apertures 43 of plate 40 of spreader assembly 2 (see FIG. 1) within hypothetical target squares 103 of coating-ready surface 102 of substrate 101. Sled-type coating apparatus 1 (see FIG. 1) is movable between starting position 120 and finish position 130 and is so moved during a method of the second embodiment.

Operate sled-type coating apparatus 1 in a method of the second embodiment as follows. Referring again to FIGS. 2A and 2B, dispose sled-type coating apparatus 1 above coating-ready surface 102 of substrate 101 so that contoured drawdown blades 30 (see FIG. 1) of spreader assembly 2 (see FIG. 1) are spaced apart from coating-ready surface 102 by approximately the distance t (not indicated) equal to thickness of shims 4 (see FIG. 1) and such that apertures 43 of plate 40 of spreader assembly 2 (see FIG. 1) are disposed directly above hypothetical target squares 103 of coating-ready surface 102 of substrate 101. When sled-type coating apparatus 1 is disposed as shown in FIG. 2A, dispense at least four liquid coating precursors (not shown), each through a different one of at least four apertures 43, at least two of the four apertures 43 being disposed in different rows, different columns, or both of the 4-row-by-5-column predefined array thereof in plate 40, and each within a different hypothetical target square 103 on the coating-ready surface 102 to give a precursor-prepared substrate (not shown). Secure either the precursor-prepared substrate (not shown) against movement relative to sled-type coating apparatus 1, or vice versa. Move sled-type coating apparatus 1 (see FIG. 1) in direction of leading faces 27 (i.e., in a left-to-right direction for the orientation shown in FIG. 1) of spacer-receiving members 20 (see FIG. 1) and cross-brace members 25 (see FIG. 1) relative to the precursor-prepared substrate so that leading surfaces 31 (see FIG. 1) of at least two contoured drawdown blades 30 (see FIG. 1) make substantially simultaneous initial contact with the liquid coating precursors (not shown), and spread the dispensed liquid coating precursors (not shown) into test coatings (not shown) within hypothetical target squares 103 on coating-ready surface 102 of substrate 101, thereby forming at least four test coatings (not shown) on coating-ready surface 102 of substrate 101, the test coatings (not shown) being disposed thereon in the two-dimensional arrangement (not shown) and, preferably, substantially within different ones of hypothetical target squares 103. When sled-type coating apparatus 1 is disposed as shown in FIG. 2A, dispensing 20 liquid coating precursors (not shown) through a different one of each of apertures 43 of plate 40 and within a different hypothetical target square 103 on the coating-ready surface 102 of substrate 101 will provide the precursor-prepared substrate (not shown) having a 4-row-by-5-column predefined array of the liquid coating precursors (not shown) dispensed thereon. Alternatively when sled-type coating apparatus 1 is disposed as shown in FIG. 2A, dispensing the 20 liquid coating precursors (not shown) as just described and dispensing an additional four liquid coating precursors (not shown) within remaining right-most column (not indicated) of four hypothetical target squares 103 on the coating-ready surface 102 of substrate 101 will provide the precursor-prepared substrate (not shown) having a 4-row-by-6-column predefined array of the liquid coating precursors (not shown) dispensed thereon.

Figure 3:
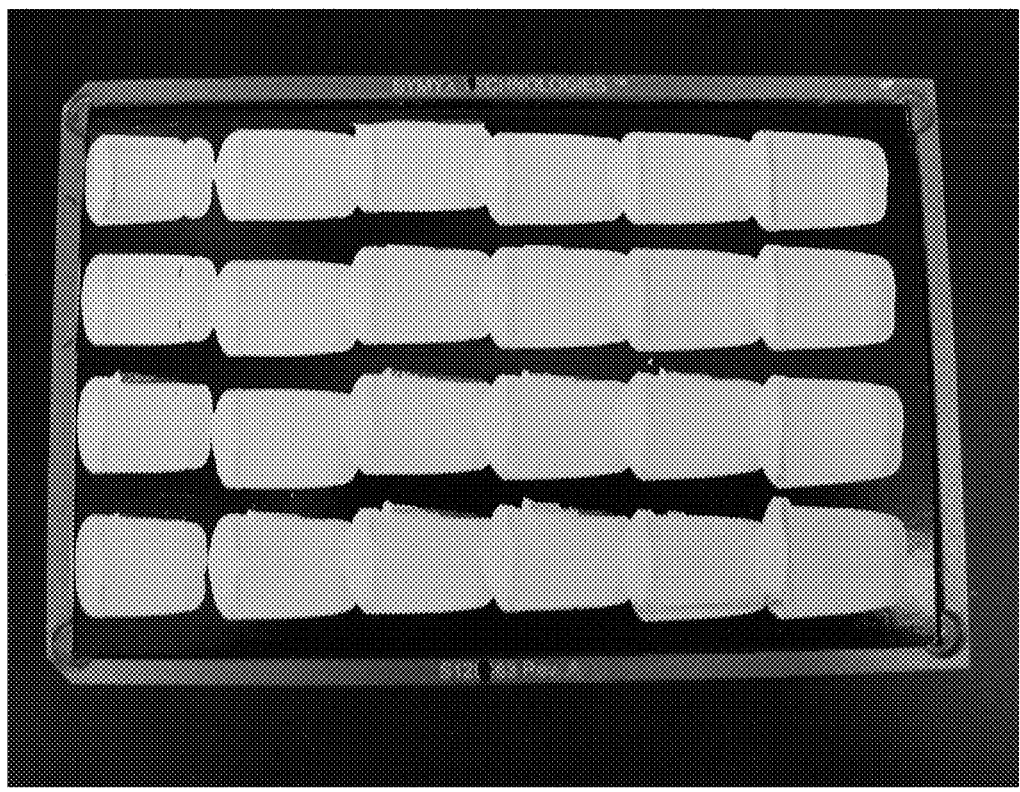
FIG. 3 is a black-and-white photographic image of a 4-row-by-6-column predefined array of 24 latex paint test coatings formed on a substrate according to a preferred embodiment of the method of the second embodiment.

As mentioned previously, FIG. 3 is a black-and-white photographic image of a 4-row-by-6-column predefined array of 24 latex paint test coatings (not indicated) formed using sled-type coating apparatus 1 (see FIG. 1) on a substrate (not indicated) according to a preferred embodiment of the method of the second embodiment. In FIG. 3, the latex paint test coatings (not indicated) have been formed by spreading a liquid coating precursor that is a latex paint (not shown) from left-to-right.

FIG. 4 is described later in the Examples.

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, any lower limit of a range of numbers, or any preferred lower limit of the range, may be combined with any upper limit of the range, or any preferred upper limit of the range, to define a preferred aspect or embodiment of the range. Each range of numbers includes all numbers, both rational and irrational numbers, subsumed within that range (e.g., the range from about 1 to about 5 includes, for example, 1, 1.5, 2, 2.75, 3, 3.80, 4, and 5).

In an event where there is a conflict between a compound name and its structure, the structure controls.

In an event where there is a conflict between a unit value that is recited without parentheses, e.g., 2 inches, and a corresponding unit value that is parenthetically recited, e.g., (5 centimeters), the unit value recited without parentheses controls.

As used herein, "a," "an," "the," "at least one," and "one or more" are used interchangeably. In any aspect or embodiment of the instant invention described herein, the term "about" in a phrase referring to a numerical value may be deleted from the phrase to give another aspect or embodiment of the instant invention. In the former aspects or embodiments employing the term "about," preferably it means from 90 percent to 100 percent of the numerical value, from 100 percent to 110 percent of the numerical value, or from 90 percent to 110 percent of the numerical value. In any aspect or embodiment of the instant invention described herein, the open-ended terms "comprising," "comprises," and the like (which are synonymous with "including," "having," and "characterized by") may be replaced by the respective partially closed phrases "consisting substantially of," consists substantially of," and the like or the respective closed phrases "consisting of," "consists of," and the like to give another aspect or embodiment of the instant invention. In the present application, when referring to a preceding list of elements (e.g., ingredients), the phrases "mixture thereof," "combination thereof," and the like mean any two or more, including all, of the listed elements. The term "or" used in a listing of members, unless stated otherwise, refers to the listed members individually as well as in any combination, and supports additional embodiments reciting any one of the individual members (e.g., in an embodiment reciting the phrase "10 percent or more," the "or" supports another embodiment reciting "10 percent" and still another embodiment reciting "more than 10 percent."). The term "plurality" means two or more, wherein each plurality is independently selected unless indicated otherwise. Weight percent (wt %) of a material is based on total weight of the material unless otherwise noted.

The term "liquid coating precursor" means a mechanically spreadable mixture comprising a material that can form a solid upon drying or curing and a solvent (e.g., water). Examples of the material that can form a solid are finely divided solids (e.g., pigment) and two liquid materials (e.g., a glycidyl ether-containing epoxy resin and a curing agent such as an amine or anhydride) that can react (e.g., during curing)

to form the solid. The mechanically spreadable mixture may further comprise other ingredients such as, for example, a binder. An example of a liquid coating precursor is a paint comprising a latex, binder, and one or more additional paint additives such as pigments and tints.

The term "substantially simultaneously" means overlapping in time.

The term "substrate" means a homogeneous or heterogeneous (e.g., composite) material having a coating-ready surface (e.g., 102) disposed for having spread thereon the at least four test coatings. Preferably, form of the material comprises a sheet. The coating ready surface can be monolithic (e.g., with a homogeneous material, substantially monolithic (e.g., with a uniformly dispersed heterogeneous material), or non-monolithic (e.g., a base sheet having adhered thereon two or more laminates, preferably four or more laminates in the two-dimensional arrangement, each laminate being of the same or different material as another laminate and being ready for having spread thereon one or more of the at least four coating precursors). Examples of suitable substrate materials are metal (e.g., aluminum), metal alloy (e.g., a stainless steel), homopolymer (e.g., polypropylene), a copolymer (e.g., poly(styrene butadiene), concrete, glass, and testing charts such as those that can be purchased from The Leneta Company, Inc., Mahwah, N.J., USA.

The term "test coating" means a layer of a substance on a substrate, preferably the substance comprising a dried or cured liquid coating precursor. The layer of the substance can be, for example, a film, surface treatment (e.g., a chemical etching), protective layer, adhesive layer, varnish layer, or paint layer. A test coating can also mean a coating of a dirt (e.g., bituminous coal dust) or stain (e.g., ketchup, mustard, coffee, and red wine) applied to a substrate or test coating.

As used herein, the term "workflow" means an integrated process comprising steps of experimental design, forming a plurality of same or different coatings on a substrate, independently analyzing the coatings to determine one or more characteristics or properties thereof, and collecting data from the resulting coating analyses. In this context, the term "high throughput workflow" means the steps of the workflow are integrated and time-compressed such that an overall time to execute the integrated process of the high throughput workflow is from 2.0 times or more (e.g., 10, 50 or 100 times or more) faster than an overall time to execute a corresponding process of a standard non-high throughput workflow (e.g., any corresponding prior art process).

Each spreading means (e.g., 30) independently is capable of spreading one or more than one liquid coating precursor. Thus, there can be one spreading means per test coating or fewer, although there is at least two spreading means in each invention coating apparatus (e.g., 1). Preferably, one or more spreading means (e.g., 30) of the spreader assembly (e.g., 2) of the coating apparatus of the first embodiment (e.g., 1) preferably comprises a drawdown blade (e.g., 30), the drawdown blade being disposed approximately perpendicular to the sides (e.g., 47 and 48) and approximately parallel to, and in operative connection with, the bottom surface (e.g., 41) of the plate (e.g., 40) of the spreader assembly (e.g., 2). More preferably, at least one drawdown blade is a contoured drawdown blade (e.g., 30), the contoured drawdown blade having a leading surface (e.g., 31) disposed for contacting the substrate (e.g., 101) at an angle therebetween of from greater than 10 degrees to less than 80 degrees. Each drawdown blade is capable of spreading 2, preferably at least 3, more preferably at least 4, and even more preferably at least 8 liquid coating precursors. The plurality of drawdown blades is at least two, preferably at least 3, more preferably at least 4, still more preferably at least 5, and even more preferably at least 6.

Preferably, the spreader assembly (e.g., 2) further comprises a handle member (e.g., 50) for holding the spreader assembly for a spreading operation. The handle member (e.g., 50) can be configured conventionally such as, for example, for being gripped robotically or, preferably, manually (e.g., by hand). Where the handle member (e.g., 50) is adapted for being mounted to a robotic apparatus (not shown), the robotic apparatus comprises a means for automating movement (not shown) of the coating apparatus (e.g., 1), especially the spreader assembly (e.g., 2), and more especially the plurality of spreading means (e.g., 30) relative to the substrate (e.g., 101). Preferably, the basal support member further comprises a means to limit movement of the invention coating apparatus (e.g., 1) between a starting position (e.g., 120) and a finish position (e.g., 130).

Preferably, the spaced apart distance (e.g., t, not shown) between the substrate (e.g., 101), i.e., the coating-ready surface (e.g., 102) thereof, and the plurality of spreading means (e.g., 30) is adjustable by varying the spacer (e.g., 4). The spacer (e.g., 4) can be varied by conventional means such as, for example, increasing or decreasing its height or thickness (e.g., by inflation or deflation of an inflatable spacer or swelling or reducing swelling of a swellable spacer material) and replacing the spacer with a different sized (thinner or thicker) spacer.

Preferably, the invention coating apparatus (e.g., 1) further comprises a means for holding (e.g., 110) the substrate (e.g., 101) in a fixed position relative to the invention coating apparatus (e.g., 1), or vice versa. Examples of suitable means for holding are a frame (e.g., 110), vacuum assembly means (not shown), a carrier (e.g., a Hamilton robot carrier), or a combination thereof. Preferably, the means for holding comprises a frame (e.g., 110) or, more preferably, a vacuum assembly means (not shown) for holding the substrate. Where the invention coating apparatus (e.g., 1) is adapted for being mounted to a robotic apparatus (not shown), preferably the means for holding comprises the vacuum assembly (not shown), which preferably comprises a base plate having top and bottom surfaces and defining a plurality of apertures between the top and bottom surfaces, the bottom surface of the base plate and apertures being in fluid communication with a vacuum source.

Preferably, the liquid coating precursors are dispensed with a liquid handling robot, more preferably with a multi-tip liquid handling robot such as, for example, a Hamilton MICROLAB® STAR robot (Hamilton Company, Reno, Nev., USA). Robotic dispensing of the liquid coating precursors reduces time period for undesired drying of the dispensed liquid coating precursors before they can be spread. This undesired drying time period starts in step (b) with dispensing of a first of the liquid coating precursors and ends in the step (c) with completion of the moving the spreader assembly (e.g., 2) during a method of the second embodiment. In some embodiments, the undesired drying time period is less than 50%, more preferably less than 25%, still more preferably less than 10%, and even more preferably less than 5% of a corresponding undesired drying time period for the previously mentioned process of a standard non-high throughput workflow (e.g., any corresponding prior art process).

Each aperture (e.g., 43) in the plate (e.g., 40) independently is capable of receiving one or more than one liquid coating precursor. Thus, there can be one aperture per test coating or fewer (e.g., as in the case of an aperture being a slot (not shown) spanning between sides 47 and 48 of plate 40 and thereby replacing a row of four apertures 43), although there are at least two apertures in each invention coating apparatus (e.g., 1). Apertures (e.g., 43) can be disposed in the plate (e.g., 40) of the spreader assembly (e.g., 2) of the invention coating apparatus (e.g., 1) in a number of at least 2, wherein when there are just 2 apertures, at least 2 liquid coating precursors are dispensed through one of the 2 apertures and at least 1 liquid coating precursor is dispensed through the other of the 2 apertures. The number of the plurality of apertures (e.g., 43) disposed in the plate (e.g., 40) can be higher than, equal to, or lower than the number of the plurality of test coatings formed by the method of the second embodiment.

The number of the plurality of apertures (e.g., 43, disposed in the plate (e.g., 40) can be: less than the number of the plurality of spreading means (e.g., a slot aperture (not shown) and a row of multiple tooth-like spreading means disposed generally parallel and proximal thereto), equal to the number of the plurality of spreading means (e.g., a slot aperture (not shown) and a drawdown blade (e.g., 30) disposed generally parallel and proximal thereto), or greater than the number of the plurality of spreading means (a row of multiple apertures (e.g., 43) and a drawdown blade (e.g., 30) disposed generally parallel and proximal thereto).

The invention coating apparatus can be constructed of conventional materials known to be useful in the high throughput research apparatus art. Examples of such conventional materials are metals (e.g., titanium and aluminum), metal alloys (e.g., a stainless steel), polymers (e.g., polypropylene, poly (styrene butadiene), polytetrafluoroethylene, and a poly(ester amide)), glass (e.g., a borosilicate glass), reinforced plastic (e.g., fiberglass reinforced plastic), and combinations thereof. In some embodiments, the coating apparatus further comprises one or more other components such as, for example, gauges (e.g., pressure or temperature gauges or both), vacuum chucks, robotic carriers, vacuum pumps, and portions for making operative connections (e.g., brackets).

In the method of the second embodiment, the test coatings are formed in a two-dimensional arrangement. The term "two-dimensional arrangement" means a planar spacing of positions along an x-axis and y-axis, wherein each position independently can host either zero or one test coating provided at least 4 test coatings are formed. Preferably the two-dimensional arrangement comprises a predefined array. The term "predefined array" means a particular type of two-dimensional arrangement, wherein positions of the predefined array are separated from nearest neighbors along the x- and y-axes by predetermined spacing of positions. A smallest predefined array comprises 4 positions arranged in 2 rows and 2 columns. Any other combination of numbers of rows and columns is contemplated provided the maximum number of positions is 1000 or less. Thus, when number of one of rows and columns is 2, the maximum number of the other of rows and columns is 500. While usually capability of creating highest numbers of test coatings is desirable, for practical reasons in some embodiments the maximum number of positions and test coatings preferably is 500 or less, more preferably 250 or less, and still more preferably 200 or less. Predefined arrays are especially useful for high throughput research applications employing standardized equipment such as, for example, conventional 96-position plates in an 8-row-by-12-column predefined array. In the method of the second embodiment, there is formed a two-dimensional arrangement of test coatings comprising 3 or more, preferably 4 or more, more preferably 12 or more, and still more preferably 20 or more test coatings. For adoption in conventional high throughput research workflows, in some embodiments it is desirable to substantially simultaneously form from 12 to 96 test coatings.

Preferably, the invention method further comprises a step of (d) independently evaluating at least one characteristic or property of the test coatings. Preferably, the characteristic or property of the test coatings that is evaluated in step (d) is stain resistance, glossiness, scrub resistance, or, more preferably, dirt pick-up resistance. Still more preferably in step (d), the dirt pick-up resistance is evaluated comprising steps: (d-a) measuring an initial light reflectance of each of the test coatings; (d-b) contacting the test coatings with test materials to give corresponding contacted coatings; (d-c) rinsing the contacted coatings at least once with one or more liquids to give corresponding rinsed coatings; (d-d) measuring a final light reflectance of each of the rinsed coatings; and (d-e) for at least one of the test coatings, independently comparing the initial light reflectance for the test coating to the final light reflectance of the corresponding rinsed coating so as to evaluate dirt pick-up resistance of the test coating. Preferably, the comparing step (d-e) comprises determining percent change in light reflectance between the initial light reflectance of the test coating and the final light reflectance of the corresponding rinsed coating.

Since the plurality of test coatings are essentially simultaneously formed by the method of the second embodiment, they can be and preferably are subjected to same curing or drying conditions, rendering any data obtained in the evaluating step (d) more accurate and reproducible than data the corresponding process of the previously mentioned standard non-high throughput workflow (e.g., any corresponding prior art process). Examples of same curing or drying conditions are same amount of curing or drying time, same curing or drying temperature-time profile, and same curing or drying pressure-time profile. Curing and drying conditions independently can be carried out by conventional means such as, for example, heating (e.g, in an oven or environmental chamber), cooling (e.g., in a refrigerator), and vacuum oven drying or blow drying.

In some embodiments of the invention method, at least two of the test coatings differ in composition from each other. In some embodiments, at least two of the test coatings have the same composition as each other. In some embodiments of the invention method, at least some of the liquid coating precursors are dispensed substantially simultaneously onto the substrate. Liquid coating precursors can be dispensed by conventional means, preferably as a single drop or several drops (e.g., 3).

Preparation 1: Provide three latex paints, each comprising a pigment and a different binder, the binders being a high-solids styrene-acrylic binder (in Latex Paint (A)), a 100% acrylic polymer binder (in Latex Paint (B)), and an unknown binder (in Latex Paint (C)).

EXAMPLE(S) OF THE PRESENT INVENTION

The following example(s) are provided to further illustrate, but not limit scope of, the present invention.

Examples 1a, 1b, and 1c

Preparing Dried Test Plates of 4-Row-by-6-Column Predefined Array of 24 Test Coatings Formed from Latex Paint (A), Latex Paint (B), or Latex Paint (C), respectively Substantially simultaneous coating procedure: Select a clean white scrub panel (Leneta form P122-10-16; The Leneta Company, Inc., Mahwah, N.J., USA) as substrate and prepare thereon a 4-row-by-6-column predefined array of 24 test coatings using coating apparatus-substrate holder assembly 100 (FIGS. 2A and 2B) by aspirating about 154 μL of latex paint formulations into 1 mL-volumed tips, and then dispensing 3×18 μL drops (54 μL total for forming each test coating) of Latex Paint (A) using a Hamilton syringe onto the scrub panel. Form test coatings by drawing the dispensed latex paint down using coating apparatus 1 (FIG. 1) having a shim 4 thickness, and thus distance t between contoured drawdown blades 30 and the scrub panel of about 10 mils (0.254 millimeter). Allow the test coatings to dry at room temperature (about 25° C.) and pressure (about 101 kilopascals) for about 5 to 7 days to give a dried test plate comprising 24 test coatings of one of the latex paints. Repeat once so that Latex Paint (A) is used to form a total of two dried test plates, each having 24 test coatings of Latex Paint (A). Follow the procedure of Example 1a except using Latex Paint (B) or (C) instead of Latex Paint (A) to prepare two dried test plates with Latex Paint (B) and two dried test plates with Latex Paint (C). Reflectance measurement procedure: Measure initial color of each of 24 test coatings on each dried test plate using an automated colorimeter comprising an Ocean Optics ISP-REF integrating sphere with a 0.4 inch (1.0 centimeter) sampling aperture operatively connected via a fiber optic cable to an Ocean Optics USB 4000 spectrometer (Ocean Optics Inc., Dunedin, Fla., USA). Perform the color measurements with D65/10° illumination.

Examples 2a, 2b, and 2c

Evaluate Dirt Pick-Up Resistance of Each Test Plate of 24 Test Coatings from Latex Paint (A), Latex Paint (B), or Latex Paint (C), Respectively Dirt treatment: Prepare a 50 wt % dirt and water mixture, and stir it with a wooden spatula, wherein the dirt is bituminous coal dust (other dirt can be used). Place the dirt and water mixture in a Flack Tech Inc. speed mixer, spin for 1.5 minutes at 2500 revolutions per minute (rpm), stir by hand, and repeat spinning to give spun dirt/water mixture. Aspirate 250 μL of the spun dirt/water mixture into each of 8 pipettes, and dispense using the previously mentioned Hamilton MICROLAB® STAR robot three 16 μL (48 μL total) aliquots per test coating on one of the dried test plates of 24 test coatings of Latex Paint (A) of Example 1a. Dry the resulting dirt deposition for 3 hours at room temperature and pressure, then rinse the resulting dried dirt depositions with a total of two aliquots of 300 mL of distilled water. Dry the resulting treated and rinsed test coatings overnight, and measure their color using the aforementioned automated colorimeter. With the same test plate, repeat the dirt treatment procedure three more times for a total of four treatment cycles per dirt-treated test plate. Repeat the procedure with the other dried test plate of 24 test coatings from Latex Paint (A) to give another total of four treatment cycles. Follow the procedure of Example 2a except use the 2 test plates of 24 test coatings of Example 1b or 1c to give two groups a total of four treatment cycles for Examples 1b and 1c, respectively.

FIG. 4 shows plots of an average of percent drop in reflectance for measurements taken on the 24 test coatings of each of the six total dirt-treated test plates of Examples 2a to 2c over four dirt treatment cycles. The plots show reflectance decreases with each dirt treatment cycle. The plots also show differences in reflectance in a particular cycle that may be due to experimental differences (e.g., in dirt coverage or rinsing variations) decrease with increasing number of cycles, and thus any error due to such experimental differences can be minimized.

As shown by the Examples, the coating apparatus and method of the first and second embodiments, respectively, provide a means of substantially simultaneously forming a plurality of test coatings on a substrate, including using a high throughput coating workflow. The invention method further provides a means of analyzing at least one characteristic or property of the test coatings in a high throughput coating analysis workflow. The Example test coatings on the test plates can be used as, for example, commercial display samples (e.g., of paint colors as illustrated in FIG. 3); as materials for analysis in coating research and development (e.g., analysis of characteristics such as, for example, color and gloss, of physical properties such as, for example, degree of hardness and resistance to cracking (e.g., mud cracking, minimum film formation temperature, and low temperature coalescence), of chemical properties such as, for example, adhesive bonding strength, blocking, solubility, dirt pick-up resistance, and stain resistance, or of a combination thereof); and as adhesive applications for bonding the substrate to another material.

While the present invention has been described above according to its preferred aspects or embodiments, it can be modified within the spirit and scope of this disclosure. This application is therefore intended to cover any variations, uses, or adaptations of the present invention using the general principles disclosed herein. Further, the application is intended to cover such departures from the present disclosure as come within the known or customary practice in the art to which this present invention pertains and which fall within the limits of the following claims.

What is claimed is:

1. A coating apparatus, the coating apparatus being for substantially simultaneously forming a plurality of coatings on a substrate, the coatings being disposed in a two-dimensional arrangement thereon, the coating apparatus comprising a spreader assembly, basal support member, and one or more spacers, wherein:
   (a) the spreader assembly is for substantially simultaneously spreading at least four liquid coating precursors in a two-dimensional arrangement on a substrate, the spreader assembly comprising a plate and a plurality of spreading means:
      (i) the plate having spaced apart top and bottom surfaces, spaced apart sides, and defining a plurality of apertures therethrough between the top and bottom surfaces, the apertures being disposed in a two-dimensional arrangement and dimensioned for allowing dispensing of the liquid coating precursors through the apertures in the plate and onto the substrate and the plurality of spreading means being less than, equal to, or greater than the plurality of apertures in the plate, and
      (ii) the plurality of spreading means extending downwardly from the bottom surface of, and being in operative connection with, the plate so that each spreading means, or a portion thereof, is disposed proximal to a different one of the apertures, or a portion thereof, in the plate;
   (b) the basal support member comprising a guide member for defining a coating direction, the basal support member defining at least one through-hole therein, the at least one through-hole being disposed for receiving the plurality of spreading means of the spreader assembly; and (c) each spacer being disposed in direct physical contact with the spreader assembly and the basal support member, thereby establishing a spaced-apart distance between the substrate and the plurality of spreading means.

2. The coating apparatus as in claim 1 wherein one or more of the spreading means comprises a drawdown blade, the drawdown blade being disposed approximately perpendicular to the sides and approximately parallel to, and in operative connection with, the bottom surface of the plate of the spreader assembly.

3. The coating apparatus as in clam 2 wherein at least one drawdown blade is a contoured drawdown blade, the contoured drawdown blade having a leading surface disposed for contacting the substrate at an angle therebetween of from greater than 10 degrees to less than 80 degrees.

4. The coating apparatus as in claim 1 wherein the spreader assembly further comprises a handle member for holding the spreader assembly for a spreading operation.

5. The coating apparatus as in claim 4 wherein the handle member is adapted for being mounted to a robotic apparatus, the robotic apparatus comprising a means for automating movement of the coating apparatus relative to the substrate.

6. The coating apparatus as in claim 1 wherein the basal support member further comprises a means to limit movement of the coating apparatus between a starting position and a finish position.

7. The coating apparatus as in claim 1 wherein the spaced apart distance between the substrate and the plurality of spreading means is adjustable by varying the spacer.

8. The coating apparatus as in claim 1, the coating apparatus further comprising a vacuum assembly means for holding the substrate in a fixed position.

9. The coating apparatus as in claim 1 wherein the two-dimensional arrangement of apertures in the plate of the spreader assembly comprises a predefined array.

10. A method of substantially simultaneously forming a plurality of test coatings on a substrate, the test coatings being disposed in a two-dimensional arrangement thereon, the method comprising steps of:
(a) disposing a coating apparatus above a coating-ready surface of a substrate;
wherein the coating apparatus comprises a spreader assembly, basal support member, and one or more spacers, wherein:
(1) the spreader assembly is for substantially simultaneously spreading at least four liquid coating precursors in a two-dimensional arrangement on a substrate, the spreader assembly comprising a plate and a plurality of spreading means:
(i) the plate having spaced apart top and bottom surfaces, spaced apart sides, and defining a plurality of apertures therethrough between the top and bottom surfaces, the apertures being disposed in a two-dimensional arrangement and dimensioned for allowing dispensing of the liquid coating precursors through the apertures in the plate and onto the substrate and the plurality of spreading means being less than, equal to, or greater than the plurality of apertures in the plate, and
(ii) the plurality of spreading means extending downwardly from the bottom surface of, and being in operative connection with, the plate so that each spreading means, or a portion thereof, is disposed proximal to a different one of the apertures, or a portion thereof, in the plate;
(2) the basal support member comprising a guide member for defining a coating direction, the basal support member defining at least one through-hole therein, the at least one through-hole being disposed for receiving the plurality of spreading means of the spreader assembly; and
(3) each spacer being disposed in direct physical contact with the spreader assembly and the basal support member, thereby establishing a spaced-apart distance between the substrate and the plurality of spreading means.
(b) dispensing through apertures of the spreader assembly of the coating apparatus at least four liquid coating precursors onto the coating-ready surface of the substrate to give a precursor-prepared substrate having the at least four liquid coating precursors dispensed thereon in a two-dimensional arrangement; and
(c) moving the spreader assembly of the coating apparatus relative to the precursor-prepared substrate so as to substantially simultaneously contact and spread the liquid coating precursors on the coating-ready surface of the substrate, thereby forming at least four test coatings on the coating-ready surface of the substrate, the test coatings being disposed thereon in the two-dimensional arrangement.

11. The method as in claim 10, the method further comprising a step of (d) independently evaluating at least one characteristic or property of the test coatings.

12. The method as in claim 11, wherein the characteristic or property of the test coatings that is evaluated in step (d) is dirt pick-up resistance.

13. The method as in claim 12, wherein in step (d), the dirt pick-up resistance is evaluated comprising steps:
(d-a) measuring an initial light reflectance of each of the test coatings;
(d-b) contacting the test coatings with test materials to give corresponding contacted coatings;
(d-c) rinsing the contacted coatings at least once with one or more liquids to give corresponding rinsed coatings;
(d-d) measuring a final light reflectance of each of the rinsed coatings; and
(d-e) for at least one of the test coatings, independently comparing the initial light reflectance for the test coating to the final light reflectance of the corresponding rinsed coating so as to evaluate dirt pick-up resistance of the test coating.

14. The method as in claim 13, wherein the comparing step (d-e) comprises determining percent change in light reflectance between the initial light reflectance of the test coating and the final light reflectance of the corresponding rinsed coating.

15. The method as in claim 10, wherein at least two of the test coatings differ in composition from each other.

16. The method as in claim 10, wherein at least two of the test coatings have the same composition as each other.

17. The method as in claim 10, wherein at least some of the liquid coating precursors are dispensed substantially simultaneously onto the substrate.

18. The method as in claim 10, the method substantially simultaneously forming from 12 to 96 test coatings.

\* \* \* \* \*